(12) United States Patent
Regueiro-Ren et al.

(10) Patent No.: US 6,719,540 B2
(45) Date of Patent: Apr. 13, 2004

(54) C3-CYANO EPOTHILONE DERIVATIVES

(75) Inventors: Alicia Regueiro-Ren, Middletown, CT (US); Soong-Hoon Kim, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/386,072

(22) Filed: Mar. 11, 2003

(65) Prior Publication Data

US 2003/0191089 A1 Oct. 9, 2003

Related U.S. Application Data

(60) Provisional application No. 60/363,441, filed on Mar. 12, 2002.

(51) Int. Cl.$^7$ .................. C07D 493/04; A61K 31/427

(52) U.S. Cl. ......................... 417/365; 548/204

(58) Field of Search ................ 548/204; 514/365

(56) References Cited

PUBLICATIONS

Reuiero–Ren, Organic Letters 4 (22) 3815 2002.*

* cited by examiner

*Primary Examiner*—Robert Gerstl
(74) *Attorney, Agent, or Firm*—Rena Patel

(57) ABSTRACT

The present invention relates to compounds useful in the treatment of cancer or other proliferative diseases represented by formula I:

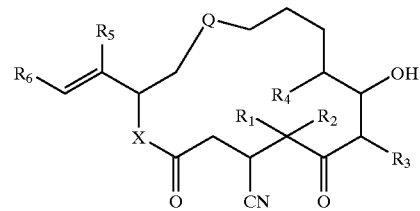

wherein:
Q is selected from the group consisting of

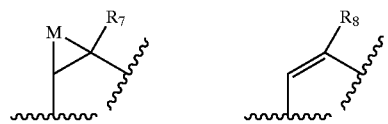

M is O, $NR_9$, or $CR_{10}R_{11}$; X is O or NH; and the R groups are as defined, and therapeutic compositions containing them alone or in combination with other therapeutic agents useful in the treatment of cancer or other proliferative diseases.

35 Claims, No Drawings

C3-CYANO EPOTHILONE DERIVATIVES

CROSS-REFERENCE TO RELATED APPLICATION

This application claims priority from provisional application serial No. 60/363,441, filed Mar. 12, 2002, incorporated herein by reference in its entirety.

FIELD OF THE INVENTION

The present invention relates to 3-cyano substituted macrolide compounds possessing anti-tumor activity, methods for the preparation of the compounds, pharmaceutical compositions containing the compounds and methods of using these compounds.

BACKGROUND OF THE INVENTION

Epothilones are macrolide compounds which find utility in the pharmaceutical field. For example, Epothilones A and B having the structures:

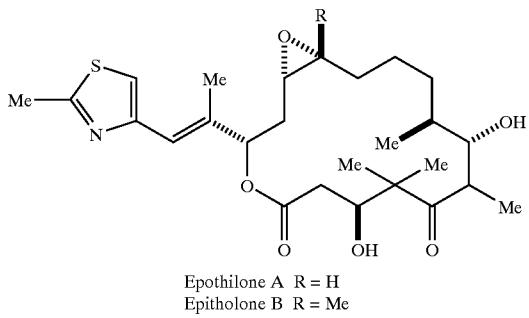

Epothilone A R = H
Epitholone B R = Me may be found to exert microtubule-stabilizing effects similar to paclitaxel (TAXOL®) and hence cytotoxic activity against rapidly proliferating cells, such as, tumor cells or other hyperproliferative cellular disease, see Hofle, G., et al., Angew. Chem. Int. Ed. Engl., Vol. 35, No.13/14, 1567–1569 (1996); WO93/10121 published May 27, 1993; and WO97/19086 published May 29, 1997.

The widespread interest in epothilones that originated with the discovery of their mircotubulin-stabilization activity was furthered by the finding that epothilones were active in vitro against a number of paclitaxel-resistant human cancer cell lines (Bollag, D. M., et al., Cancer Res., Vol. 55, 2325–2333 (1995); Kowalski, R. J., et al., J. Biol. Chem., Vol. 272, 2534–2541 (1997)). Additionally, the relatively efficient total synthesis of epothilones, compared to that of paclitaxel, has lead to extensive efforts in the synthesis of epothilone analogs, as well as the characterization of their biological activity and strutcure/activity relationship (SAR) features. (Altmann, K.-H., et al., Curr. Opin. Chem. Biol., Vol. 5, 424–431 (2001)).

Several groups have been active in this area including Danishefsky at the Memorial Sloan-Kettering Cancer Research Center, Nicolaou at the Scripps Research Institute, Altmann at Novartis Pharma AG and Klar at Shering AG. For example, the Danishefsky group has prepared and characterized the biological activity of 12,13-desoxyepothilone derivatives (Chou T.-C. et al., Proc. Natl. Acad. Sci., Vol. 95, 9642 (1998)). The Nicolaou group at the Scripps Research Institute has synthesized 12,13-cyclopropyl, 12,13-cyclobutyl and related pyridine side-chain epothilone analogs. (Nicolaou, K. C., J. Amer. Chem. Soc., Vol. 123, 9313–9323 (2001)). Epothilone derivatives containing 16-halo substitutions have been prepared by the group at Schering AG (WO 00/49021). Additionally, Altmann at Novartis Pharma AG has synthesized an epothilone analog in which the thiazole moitey is conformationally locked by a benzenoid functionality (Altmann, K.-H. et al., Chimica, Vol. 54, No. 11,612–621 (2000)).

Examples of C-3 substituted Epothilone compounds are those possessing an ether, halo or sulfonyl group (see Schering AG, WO 00/66589); or where C-2 and C-3 together form a double bond (see Novartis, WO 00/25929 and WO 00/37473).

Derivatives and analogs of Epothilones A and B have been synthesized and tested against a variety of cancers and other abnormal proliferative diseases. Such analogs are disclosed in Hofle, G., et al., Angew. Chem. Int. Ed. Engl., Vol. 35, No.13/14, 1567–1569 (1996); Nicolaou, K. C., et al., Angew. Chem. Int. Ed. Engl., Vol. 36, No. 19, 2097–2103 (1997); Su, D.-S., et al., Angew. Chem. Int. Ed. Engl., Vol. 36, No. 19, 2093–2097 (1997); Su, D.-S., et al., Angew. Chem. Int. Ed. Engl., Vol. 36, 757–759 (1997); Meng, D., et al., J. Amer. Chem. Soc., Vol. 119, 10073–10092 (1997); Yang, Z., et al., Angew. Chem. Int. Ed. Engl., Vol. 36, 166–168 (1997); Nicolaou, K. C., et al., Angew. Chem. Int. Ed. Engl., Vol. 36, 525–527 (1997); Nicolaou, K. C., et al., Nature, Vol. 387, 268–272 (1997); Schinzer, D., et al., Angew. Chem. Int. Ed. Engl., Vol. 36, 523–524 (1997); and Nicolaou, K. C., et al., Angew. Chem. Int. Ed. Engl., Vol. 37, 2014–2045 (1998). Although natural product epothilones A and B have shown excellent in vitro cytotoxic activity against cancer cell lines, difficulties remain with respect to their in vivo use due to a lack of stability, including metabolic stability, and potential toxicity (Lee, F., et al., Clin. Can. Res., Vol. 7, 1429–1437 (2001)). Thus, there remains a need in the art for biologically active epothilone compounds with improved stability and improved safety profiles.

SUMMARY OF THE INVENTION

The present invention is directed to novel epothilone compounds possessing anti-proliferative and anti-neoplastic activity, and to methods for preparation of these compounds. Further, the invention encompasses pharmaceutical containing compounds of the invention. The invention further comprises treating or preventing proliferative diseases or disorders and primary or metastatic cancer using the compounds of the present invention. The compounds of the present invention are particularly useful for treating or preventing cancers that are responsive to microtubule-stabilization agents.

In one embodiment, the invention relates to compounds which may generally be classified as "3-cyano epothilone compounds"; having the following formula:

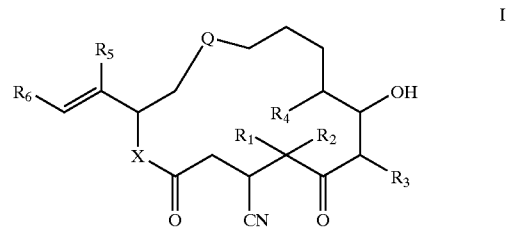

wherein

Q is selected from the group consisting of

M is O, $NR_9$, $CR_{10}R_{11}$;
X is O or NH;
$R_1$, $R_2$, $R_3$, $R_4$ and $R_5$ are independently selected from the group consisting of hydrogen or lower alkyl;
$R_6$ is selected from the group consisting of aryl, substituted aryl, and heterocyclo;
$R_7$ and $R_8$ are selected from the group consisting of hydrogen, alkyl, substituted alkyl, and cyano;
$R_9$ is selected from the group consisting of hydrogen, hydroxy, alkyl, substituted alkyl, alkoxy, substituted alkoxy, substituted aryl, cycloalkyl, heterocyclo, —C(=O) $R_{12}$, —C(=O)O$R_{13}$, —S($O_2$)$R_{14}$, —C(=O)N$R_{15}R_{16}$, —S($O_2$)N$R_{17}R_{18}$, and —N$R_{19}R_{20}$;
$R_{10}$ and $R_{11}$ are independently selected from the group consisting of hydrogen, halogen, hydroxy, alkyl, substituted alkyl, alkoxy, substituted alkoxy, aryl, substituted aryl, cycloalkyl, heterocyclo, —C(=O)$R_{21}$, —C(=O)O$R_{22}$, —C(=O)NH$R_{23}$, and —N$R_{24}R_{25}$; and
$R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$ are independently selected from the group consisting of hydrogen, alkyl, substituted alkyl, aryl, substituted aryl, and heterocyclo with the proviso that
$R_{13}$ and $R_{14}$ cannot be hydrogen;
$R_{15}$ and $R_{16}$, $R_{17}$ and $R_{18}$, $R_{19}$ and $R_{20}$, $R_{24}$ and $R_{25}$ can each independently be taken together to form a heterocyclic ring; and
isomers, clathrates, prodrugs, pharmaceutically acceptable salts, solvates or hydrates thereof.

In another embodiment, the present invention relates to methods for treating a variety of conditions by administering a therapeutically or prophylactically effective amount of a compound of formula (I) to an animal, preferably a mammal, especially a human subject in need thereof (referred to herein as a "patient"). Prior to administration, one or more compounds of this invention are typically formulated as a pharmaceutical composition which contains an effective dosage amount of one or more of such compounds in combination with one (or more) pharmaceutically acceptable carrier(s) or vehicle(s).

In another embodiment, the present invention is directed to methods of inducing microtubule-stabilization in mammalian cells by contacting the cells with a compound of the present invention.

Conditions that may be treated or prevented by the compounds of this invention, or a pharmaceutical composition thereof, include but are not limited to primary cancers, metastatic cancers, solid tumors, and blood-borne tumors. In one embodiment, the present invention is directed to methods of treating and/or preventing cancers of the brain, breast, central nervous system, stomach, bladder, prostate, colon, rectum, liver, lung (both small cell and non-small cell), pancreas, esophagus, mouth, pharynx, kidney, bone, pituitary, ovary, uterine, skin, head and neck, cervix and larynx.

In another embodiment, the present invention further provides pharmaceutical compositions comprising a therapeutically effective or a prophylactically effective amount of one or more compounds of the invention and a pharmaceutically acceptable carrier or vehicle. A pharmaceutically acceptable carrier or vehicle can comprise an excipient, diluent, or a mixture thereof.

The compounds and pharmaceutical compositions described herein could also be useful in combination therapy with other anti-cancer/cytoxic agents, angiogenesis inhibitors, anti-cancer vaccines and antibody based treatments. Additionally, the compounds and pharmaceutical compositions described herein could be useful as an adjunct to existing and/or experimental therapies. The compounds of the present invention can also used in combination with chemotherapy or irradiation therapy.

Methods of administration include but are not limited to oral, parenteral, mucosal and topical; such modes of administration further include intramuscular, intraperitoneal, intravenous, subcutaneous, intracerebral, epidural, sublingual, buccal, rectal, vaginal, intranasal, intraocular, oral, and transdermal. Preferably, the pharmaceutical compositions are formulated for injection. Preferably, oral administration will be in combination with an antacid or other suitable buffer effective at neutralizing the acidity of the stomach.

These and other aspects of this invention will be evident upon reference to the following detailed description. To that end, certain patent and other documents are cited herein to more specifically set forth various aspects of this invention. Each of these documents are hereby incorporated by reference in their entirety.

DETAILED DESCRIPTION OF THE INVENTION

The Compounds

In one embodiment, the present invention is directed to chemically and biologically stable epothilone analogs or derivatives having a 3-cyano substituent. Examples of such epothilone analogs or derivatives that may be modified to contain a 3-cyano substituent include those found in the following U.S. Pat. Nos.: 4,272,525; 4,820,695; 5,545,624; 5,610,178; 5,677,287; 5,716,939; 5,760,011; 6,034,070; 6,090,601; 6,121,029; 6,124,453; 6,204,388; 6,211,412; 6,262,094; and 6,291,684, each of which is incorporated in its entirety by reference herein. Additional examples of epothilone comounds that may be substituted in the 3-position with a cyano substituent include those found in International Publication Nos. WO 00/43320, WO 00/01701, WO 00/01702, WO 00/23452, WO 00/26349, WO 00/31247, WO 00/37473, WO 00/39276, WO 00/47584, WO 00/49019, WO 00/49020, WO 00/49021, WO 00/50423, WO 00/57874, WO 00/63224, WO 00/63225, WO 00/66589, WO 00/71521, WO 00/71556, WO 01/07439, WO 01/09113, WO 01/27308, WO 96/09312, WO 92/19247, WO 93/10121, WO 94/21657, WO 95/02594, WO 96/26182, WO 97/19086, WO 97/38009, WO 98/02460, WO 98/03662, WO 98/08505, WO 98/08849, WO 98/22461, WO 98/24427, WO 98/25929, WO 98/38192, WO 98/47891, WO 98/54966, WO 99/01124, WO 99/02514, WO 99/03848, WO 99/03849, WO 99/07692, WO 99/12906, WO 99/16416, WO 99/27890, WO 99/43653, WO 99/44619, WO 99/54318, WO 99/54319, WO 99/54330, WO 99/58534, WO 99/61599, WO 99/65884, WO 99/65913, WO 99/66028, WO 99/67252 and WO 99/67253, each of which is incorporated in its entirety by reference herein. In other words, the invention encompasses active and stable 3-cyano substituted epothilone compounds. In one embodiment, active compounds include those demonstrating useful microtubulin stabilization activity. Stable compounds include those which are not readily degraded by exposure to acid in the stomach. Examples of 3-cyano epothilone compounds and their preparation are provided below.

In one embodiment, the present invention provides 3-cyano compounds having the general formula:

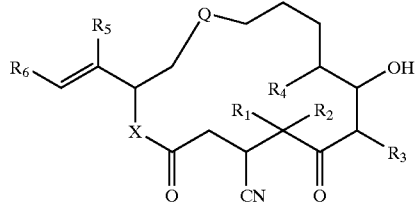

I wherein:

Q is selected from the group consisting of

M is O, $NR_9$, $CR_{10}R_{11}$;

X is O or NH;

$R_1$, $R_2$, $R_3$, $R_4$ and $R_5$ are independently selected from the group consisting of hydrogen or lower alkyl;

is $R_6$ is selected from the group consisting of aryl, substituted aryl, and heterocyclo;

$R_7$ and $R_8$ are selected from the group consisting of hydrogen, alkyl, substituted alkyl, and cyano;

$R_9$ is selected from the group consisting of hydrogen, hydroxy, alkyl, substituted alkyl, alkoxy, substituted alkoxy, substituted aryl, cycloalkyl, heterocyclo, —C(=O) $R_{12}$, —C(=O)$OR_{13}$, —S($O_2$)$R_{14}$, —C(=O)$NR_{15}R_{16}$, —S($O_2$)N$R_{17}R_{18}$, and —$NR_{19}R_{20}$;

$R_{10}$ and $R_{11}$ are independently selected from the group consisting of hydrogen, halogen, hydroxy, alkyl, substituted alkyl, alkoxy, substituted alkoxy, aryl, substituted aryl, cycloalkyl, heterocyclo, —C(=O)$R_{21}$, —C(=O)$OR_{22}$, —C(=O)NH$R_{23}$, and —$NR_{24}R_{25}$; and $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$ are independently selected from the group consisting of hydrogen, alkyl, substituted alkyl, aryl, substituted aryl, and heterocyclo with the proviso that $R_{13}$ and $R_{14}$ cannot be hydrogen;

$R_{15}$ and $R_{16}$, $R_{17}$ and $R_{18}$, $R_{19}$ and $R_{20}$, $R_{24}$ and $R_{25}$ can each independently be taken together to form a heterocyclic ring; and isomers, clathrates, prodrugs, pharmaceutically acceptable salts, solvates or hydrates thereof.

The following are definitions of various terms used to describe this invention. These definitions apply to the terms as they are used throughout this specification, unless otherwise limited in specific instances, either individually or as part of a larger group.

The term "alkyl" refers to optionally substituted straight- or branched-chain saturated hydrocarbon groups having from 1 to 20 carbon atoms, preferably from 1 to 7 carbon atoms. The expression "lower alkyl" refers to optionally substituted alkyl groups having from 1 to 4 carbon atoms.

The term "substituted alkyl" refers to an alkyl group substituted by one to four or more substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "alkenyl" refers to optionally substituted unsaturated aliphatic hydrocarbon groups having from one to nine carbons and one or more double bonds. Substituents may include one or more substituent groups as described above for substituted alkyl.

The term "halogen" or "halo" refers to fluorine, chlorine, bromine and iodine.

The term "aryl" refers to monocyclic or bicyclic aromatic hydrocarbon groups having from 6 to 12 carbon atoms in the ring portion, for example, phenyl, naphthyl, biphenyl and diphenyl groups, each of which may be substituted.

The term "aralkyl" refers to an aryl group bonded to a larger entity through an alkyl group, such as benzyl.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "cycloalkyl" refers to optionally substituted saturated cyclic hydrocarbon ring systems, preferably containing 1 to 3 rings and 3 to 7 carbons per ring, which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached to a larger molecule at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "heterocycle," "heterocyclic," and "heterocyclo" include one or more substituent groups as described above for substituted alkyl or substituted aryl, and smaller heterocyclos, such as, epoxides, aziridines and the like.

The term "alkanoyl" refers to —C(O)-alkyl.
The term "substituted alkanoyl" refers to —C(O)-substituted alkyl.
The term "aroyl" refers to —C(O)-aryl.
The term "substituted aroyl" refers to —C(O)-substituted aryl.
The term "trialkylsilyl" refers to —Si(alkyl)$_3$.
The term "aryl dialkylsilyl" refers to —Si(alkyl)$_2$(aryl).
The term "diaryl alkylsilyl" refers to —Si(aryl)$_2$(alkyl).
The term "heteroatoms" shall include oxygen, sulfur and nitrogen.

The compounds of the invention, particularly of formula I, form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts are formed by reacting a compound represented by formula I in an equivalent amount of the acid in a medium in which the salt precipitates or in an aqueous medium followed by evaporation.

The compounds represented by formula I may also form salts with alkali metals such as sodium, potassium and lithium, with alkaline earth metals such as calcium and magnesium, with organic bases such as dicyclohexylamine and tributylamine, with pyridine and amino acids such as arginine, lysine and the like. Such salts can be obtained, for example, by exchanging carboxylic acid protons, if present in a compound represented by formula I, with the desired ion in a medium in which the salt precipitates or in an aqueous medium followed by evaporation. Other salts can be formed as known to those skilled in the art.

In addition, zwitterions ("inner salts") can be formed and are included within the term salts as used herein.

Prodrugs and solvates of the compounds represented by formula I are also contemplated herein. The term prodrug, as used herein, denotes a compound which, upon administration to a subject, undergoes chemical conversion by metabolic or chemical processes to yield a compound represented by formula I, or a salt and/or solvate thereof. For example, compounds represented by formula I may form a carboxylate ester moiety that may be hydrolyzed after ingestion. The carboxylate esters are conveniently formed by esterifying any of the carboxylic acid moieties present on the molecule. Solvates of the compounds of formula I are preferably hydrates.

Various forms of prodrugs are well known in the art and have been extensively reviewed in the literature. Such prodrug delivery derivatives are discussed, for example, in the following:

a) *Design of Prodrugs*, H. Bundgaard (editor), Elsevier (1985);

b) *Methods in Enzymology*, K. Widder et al. (editors), Academic Press, Vol. 42, 309–396 (1985);

c) *A Textbook of Drug Design and Development*, Krosgaard-Larsen and H. Bundgaard (editors), Chapter 5, "Design and Application of Prodrugs," 113–191 (1991);

d) H. Bundgaard, *Advanced Drug Delivery Reviews*, 8, 1–38 (1992);

e) H. Bundgaard, *J. of Pharm. Sciences*, 77, 285 (1988); and f) N. Kakeya et al., *Chem. Pharm. Bull.*, 32 692 (1984).

The compounds of the invention may exist as multiple optical, geometric, and stereoisomers. While the compounds shown herein are depicted for one optical orientation, included within the present invention are all isomers and mixtures thereof.

Preferred compounds represented by formula I

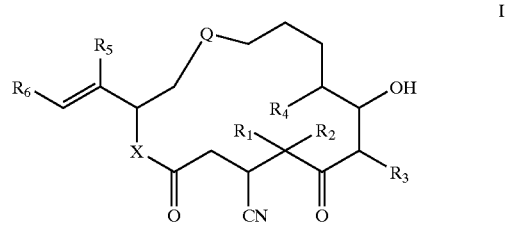

are those wherein:

Q is selected from the group consisting of:

M is O, $NR_9$, $CR_{10}R_{11}$;

X is O or NH;

$R_1$, $R_2$, $R_3$, $R_4$ and $R_5$ are independently selected from the group consisting of hydrogen or lower alkyl;

$R_6$ is a heterocyclic group as defined herein including but not limited to:

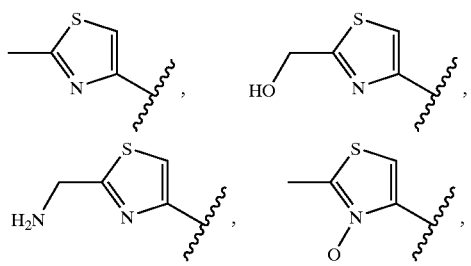

pyrrolidinyl, pyrrolyl, indolyl, pyrazolyl, imidazolyl, oxazolyl, oxazolidinyl, thiazolyl, furyl, thienyl, piperidinyl, piperazinyl, azepinyl, pyridyl, pyrazinyl, pyrimidinyl, morpholinyl, thietanyl, thiiranyl, triazinyl, and triazolyl;

$R_7$ and $R_8$ are selected from the group consisting of hydrogen, alkyl, substituted alkyl, and cyano;

$R_9$ is selected from the group consisting of hydrogen, hydroxy, alkyl, substituted alkyl, alkoxy, substituted alkoxy, substituted aryl, cycloalkyl, heterocyclo, $R_{12}C=O$, $R_{13}OC=O$, $R_{14}SO_2$, $R_{15}R_{16}NC=O$, $R_{17}R_{18}NSO_2$, and $NR_{19}R_{20}$;

$R_{10}$ and $R_{11}$ are independently selected from the group consisting of hydrogen, halogen, hydroxy, alkyl, substituted alkyl, alkoxy, substituted alkoxy, aryl, substituted aryl, cycloalkyl, heterocyclo, $R_{21}C=O$, $R_{22}OC=O$, $R_{23}NHC=O$, and $NR_{24}R_{25}$; and $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$ are independently selected from the group consisting of hydrogen, alkyl, substituted alkyl, aryl, substituted aryl, and heterocyclo with the proviso that $R_{13}$ and $R_{14}$ cannot be hydrogen;

$R_{15}$ and $R_{16}$, $R_{17}$ and $R_{18}$, $R_{19}$ and $R_{20}$, $R_{24}$ and $R_{25}$ can each independently be taken together to form a heterocyclic ring; and isomers, clathrates, prodrugs, pharmaceutically acceptable salts, solvates or hydrates thereof.

Pharmaceutical Compositions and Formulations

The present invention also provides pharmaceutical compositions comprising at least one of the compounds of the invention such as a compound represented by formula I capable of treating cancer or other proliferative diseases in an amount effective therefor, and a pharmaceutically acceptable carrier or vehicle. The compositions of the present invention may contain other therapeutic agents as described below, and may be formulated, for example, by employing conventional solid or liquid carriers or vehicles, as well as pharmaceutical additives of a type appropriate to the mode of desired administration, such as excipients, binders, preservatives, stabilizers, flavors, and the like according to techniques well known in the art of pharmaceutical formulation or called for by accepted pharmaceutical practice. The compounds represented by formula I can also be formulated in compositions such as sterile solutions or suspensions for parenteral administration. About 0.1 to 500 mg of a compound represented by formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The phrase "pharmaceutically acceptable salt(s)," as used herein includes but are not limited to salts of acidic or basic groups that may be present in compounds used in the present methods and compositions.

Exemplary compositions for oral administration include suspensions which may contain, for example, microcrystalline cellulose for imparting bulk; alginic acid or sodium alginate as a suspending agent; methylcellulose as a viscosity enhancer; sweeteners, such as fructose, aspartame or saccharin; flavoring agents, such as peppermint, oil of wintergreen; coloring agents; and preserving agents, to provide a pharmaceutically palatable preparation. Immediate release tablets which may contain, for example, one or more of microcrystalline cellulose, dicalcium phosphate, starch, magnesium stearate, lactose and other art-recognized excipients, binders, extenders, disintegrants, diluents and lubricants. Molded tablets, compressed tablets or freeze-dried tablets are exemplary forms that may be used. Exemplary compositions include those formulating the present compound(s) with fast-dissolving diluents such as mannitol, lactose, sucrose and cyclodextrins. Also included in such formulations may be high molecular weight excipients such as microcrystalline celluloses, polyethylene glycols (PEG) and the like. Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez®, available from Aldrich®), and agents to control release such as polyacrylic copolymer, carbopol and the like. Art-recognized lubricants, glidants, flavors, coloring agents and stabilizers may also be added for ease of fabrication and use. Additionally, where in tablet or pill form, the compositions may be coated to delay disintegration and absorption in the gastrointestinal tract thereby providing a sustained action over an extended period of time. Preferably, oral compositions are co-administered with an antacid to aid in neutralizing gastrointestinal fluids to prevent decomposition of the active compound(s). Selectively permeable membranes surrounding an osmotically active driving compound are also suitable for orally administered compounds or pharmaceutical compositions. In these later platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time delay material such as glycerol monostearate or glycerol stearate may also be used.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, including surfactants such as polyoxyethylated caster oil, Cremphor EL®, polysorbate 80, mannitol, 1,3-butanediol, polyethylene glycol, ethanol, water, Ringer's solution, Lactated Ringer's Solution, dextrose solutions, saline solutions such as isotonic sodium chloride solution, or other suitable dispersing or wetting and suspending agents, including synthetic mono- or diglycerides, and fatty acids, including oleic acid and the like. In one embodiment, immediately before use a compound of the present invention is reconstituted in either Sterile Water for Injection, USP, 5% Dextrose in Water ($D_5W$) or 0.9% Sodium Chloride for Injection, USP.

Exemplary compositions for rectal administration include suppositories which may contain, for example, a suitable non-irritating excipient, such as cocoa butter, synthetic glyceride esters or polyethylene glycols, which are solid at ordinary temperature, but liquify and/or dissolve in the rectal cavity to release the drug.

Exemplary compositions for topical administration include a topical carrier such as Plastibase® (mineral oil gelled with polyethylene available from Bristol-Myers Squibb Company). For example, the compounds of the invention may be administered topically to treat plaques associated with psoriasis and as such may be formulated as a cream or ointment.

When administered to a patient, the compounds are preferably in isolated form. By "isolated" it is meant that prior to administration, the compound is separated from other components of a synthetic organic chemical reaction mixture or natural product source. Preferably, the compounds are isolated via conventional techniques, e.g., extraction followed by chromatography, recrystalization, or another conventional technique.

Uses and Utility of the Compounds

The invention provides methods of treatment and/or prevention of cancers by administration to a patient a therapeutically or prophylactically effective amount of the compounds of the present invention or a pharmaceutically acceptable salt thereof.

The term "therapeutically effective amount" means the amount of a compound of the invention that will elicit the biological or medical response desired by the veterinarian or clinician that is treating diseases in the patient.

The term "prophylactically effective amount" means the amount of a compound of the present invention that will prevent or inhibit affliction or mitigate affliction of a patient with a medical condition that a veterinarian or clinician is trying to prevent, inhibit, or mitigate. Without being limited by any particular theory, the compounds of the invention, and in particular those of formula I, are believed to be primarily microtubule-stablizing agents. The compounds of the invention are useful for the treatment of a variety of cancers and other proliferative diseases including, but not limited to, the following:

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma, osteosarcoma and rhabdomyoscarcoma;

other tumors, including melanoma, seminoma, xenoderma pigmentosum, tetratocarcinoma, keratoactanthoma, neuroblastoma, thyroid follicular cancer and glioma;

tumors of the central and peripheral nervous system, including astrocytoma, neuroblastoma, glioma, and schwannomas.

Compounds of the present invention are also useful in treating or preventing cancers of the brain, breast, central nervous system, stomach, bladder, prostate, colon, rectum, liver, lung (both small cell and non-small cell), pancreas, esophagus, mouth, pharynx, kidney, bone, pituitary, ovary, uterine, skin, head and neck, cervix and larynx.

Compounds represented by formula I will also inhibit angiogenesis, thereby affecting the growth of tumors and providing treatment of tumors and tumor-related disorders. Such anti-angiogenesis properties of the compounds represented by formula I will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds of the invention as represented by formula I will induce or inhibit apoptosis, a physiological cell death process critical for normal development and homeostasis. Alterations of apoptotic pathways contribute to the pathogenesis of a variety of human diseases. Compounds represented by formula I, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Without wishing to be bound to any mechanism or morphology, compounds of the invention may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The present invention thus provides a method of treating an animal, preferably mammals and especially humans, in need of treatment for any of the aforementioned conditions, especially cancer or other proliferative diseases, comprising the step of administering to a subject in need thereof an effective amount of at least one compound represented by formula I. Other therapeutic agents such as those described below may be employed with the inventive compounds in the present method. In the method of the present invention, such other therapeutic agent(s) may be administered prior to, simultaneously with or following the administration of the compound(s) of the present invention.

Compounds of the present invention may be administered to patients who are either currently undergoing chemotherapy as well as those not undergoing chemotherapy. Compounds of the present invention may also be administered to patients who have previously undergone chemotherapy as well as those who have never undergone chemotherapy. Compounds of the present invention may be administered to patients who are either currently undergoing irradiation therapy as well as those not undergoing irradiation therapy. Compounds of the present invention may also be administered to patients who have previously undergone irradiation therapy as well as those who have never undergone irradiation therapy.

The effective amount of a compound of the present invention may be determined by methodologies well known to those skilled in the art and includes exemplary dosage amounts for a human of from about 0.05 to 200 mg/kg/day, which may be administered in a single dose or in the form of individual divided doses given, for example, up to four times per day. Preferably, the compounds are administered orally, intravenously or both, in a dosage of less than 100 mg/kg/day, in a single dose or in 2 to 4 divided doses. It will be understood that the specific dose level and frequency of dosage for any particular subject may be varied and will depend upon a variety of factors recognized by those skilled in the art including the activity of the specific compound employed, the metabolic stability and length of action of that compound, the species, age, body weight, general health, sex and diet of the subject, the mode and time of administration, rate of excretion, drug combination, and severity of the particular condition. Preferred subjects.for treatment include animals, most preferably mammals, and especially humans.

Typically, the compounds of the present invention are administered until the patient shows a response, for example, a reduction in tumor size, or until dose-limiting toxicity is observed. One of ordinary skill in the art will readily know when a patient shows a response or when dose-limiting toxicity is reached. The common dose limiting toxicities associated with compounds of formulae I and II include, but are not limited to, fatigue, arthralgia/myalgia, anorexia, hypersensitivity, neutropenia, thrombocytopenia, and neurotoxicity.

In one embodiment, the compounds of the present invention are administered by IV infusion over a period of from about 10 minutes to about 3 hours, preferably about 30 minutes to about 2 hours, more preferably about 45 minutes to 90 minutes, and most preferably about 1 hour. In particular, the methods of the invention encompass dosing protocols such as once a day for 2 to 10 days, preferably every 3 to 9 days, more preferably every 4 to 8 days and most preferably every 5 days. In one embodiment there is a period of 3 days to 5 weeks, preferably 4 days to 4 weeks, more preferably 5 days to 3 weeks, and most preferably 1 week to 2 weeks, in between cycles where there is no treatment. In another embodiment compounds of the present invention can be administered orally, intravenously, or both, once a day for 3 days, with a period of preferably 1 week to 3 weeks in between cycles where there is no treatment. In yet another embodiment compounds of the present invention can be administered orally, intravenously, or both, once a day for 5 days, with a period of preferably 1 week to 3 weeks in between cycles where there is no treatment.

In one preferred embodiment the treatment cycle for administration of compounds of the present invention is once daily for 5 consecutive days and the period between treatment cycles is from 2 to 10 days, preferably one week.

Compounds of the present invention can also be administered orally, intravenously, or both once every 1 to 10 weeks, preferably every 2 to 8 weeks, more preferably every 3 to 6 weeks, and even more preferably every 3 weeks. In one embodiment, compounds of the present invention are administered once every week. In another embodiment, compounds of the present invention are administered once every 3 weeks.

The compounds of the invention may be administered either alone or in combination with other anti-cancer and cytotoxic agents and treatments useful in the treatment of cancer or other proliferative diseases. Such agents may be administered simultaneously or sequentially with the compounds represented by formula I. Especially useful are anti-cancer and cytotoxic drug combinations wherein the second drug chosen acts in a different manner or different phase of the cell cycle, e.g., S phase, than the present compounds of formula I which exert their effects at the $G_2$—M phase. Example classes of anti-cancer and cytotoxic agents include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, bleomycin A2, bleomycin B2, peplomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as vinca alkaloids, epipodophyllotoxins, taxanes; and topoisomerase inhibitors (e.g., irinotecan); prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with chemotherapy or irradiation therapy.

Representative examples of these classes of anti-cancer/ cytotoxic agents include, but are not limited to, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, Chloroambucil, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, thiotepa, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenoloc acid, daunorubicin, deferoxamine, floxuridine, doxifluridine, ratitrexed, idarubicin, epirubican, pirarubican, zorubicin, mitoxantrone, bleomycin sulfate, mitomycin C, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, verapamil, VP-16, altretamine, thapsigargin, topotecan and any analogs or derivatives thereof.

Preferred members of the classes of anti-cancer/cytotoxic agents discussed above include, without intended limitation, paclitaxel, cisplatin, carboplatin, doxorubicin hydrochloride, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Further examples of anti-cancer and other cytotoxic agents include the following: epothilone derivatives as found in German Patent No. 4138042.8 and PCT Io International Publication Nos. WO 97/19086, WO 98/22461, WO 98/25929, WO 98/38192, WO 99/02224, WO 99/02514, WO 99/03848, WO 99/07692, WO99/27890, WO 00/43320, WO 00/01701, WO 00/01702, WO 00/23452, WO 00/26349, WO 00/31247, WO 00/37473, WO 00/39276, WO 00/47584, WO 00/49019, WO 00/49020, WO 00/49021, WO 00/50423, WO 00/57874, WO 00/63224, WO 00/63225, WO 00/66589, WO 00/71521, WO 00/71556, WO 01/07439, WO 01/09113, WO 01/27308, WO 96/09312, WO 92/19247, WO 93/10121, WO 94/21657, WO 95/02594, WO 96/26182, WO 97/38009, WO 98/02460, WO 98/03662, WO 98/08505, WO 98/08849, WO 98/24427, WO 98/47891, WO 98/54966, WO 99/01124, WO 99/03849, WO 99/07692, WO 99/12906, WO 99/16416, WO 99/43653, WO 99/44619, WO 99/54318, WO 99/54319, WO 99/54330, WO 99/58534, WO 99/61599, WO 99/65884, WO 99/65913, WO 99/66028, WO 99/67252, WO 99/67253 and WO 99/28324; cyclin dependent kinase inhibitors as found in WO 99/24416; and prenyl-protein transferase inhibitors as found in WO 97/30992 and WO 98/54966.

The compounds represented by formula I, as well as combinations thereof with the other anti-cancer/cytotoxic agents discussed above may also be formulated or co-administered with other therapeutic agents that are selected for their particular usefulness in providing certain therapies associated with the aforementioned conditions. For example, the compounds of the invention may be formulated with agents to prevent nausea, hypersensitivity, and gastric irritation, such as antiemetics, and $H_1$ and $H_2$ antihistamines. The compounds of the present invention may also be formulated with antioangiogenesis compounds, topoisomerase inhibitors and antibody formulations.

Compounds of the present invention may also be used in combination with angiogenesis antagonists. These include inhibitors of epidermal growth factor (EGF), EGF family kinases (e.g., EGF tyrosine kinases), matrix metalloproteinase (MMPs), vascular endothelial growth factor receptor (VEGFR), fibroblast growth factor receptor (FGFR) and methionine adaptor protein 2 (Met AP2). Preferred angiogenesis antagonists also include antibodies directed to angiogenesis factors.

Representative examples of these classes of angiogenesis antagonists include, but are not limited to, indolinethiones, pyridopyrimidines, quinoazolines, phenyl-pyrrolo-pyrimidines, trastuzumab, IMC-C225, AG 1571 (SU 5271), SU 5416, SU 6668, Interferon-alpha, Interleukin-12, IM 862, EMD-121974, calcium influx inhibitor (CAI), neomycin, squalamine, endostatin, SI-27, MMI-166, marimastat, BAY-129556, prinomastat (AG-3340), metastat (COL-3), CGS-27023A and BMS-275291.

The above-discussed therapeutic agents, when employed in combination with the compounds represented by formula I, may be used in their usual therapeutic dosage as given, for example, in the *Physician's Desk Reference* ($56^{th}$ ed., 2002) or as otherwise determined by the medical practitioner.

Routes of Administration

The compounds represented by formula I may be administered by any suitable means, for example, orally, such as in the form of tablets, capsules, granules or powders; sublingually; buccally; parenterally, as sterile injectable aqueous or non-aqueous solutions or suspensions, by subcutaneous, intravenous, intramuscular, or intrasternal injection or infusion techniques; nasally, such as by inhalation spray; topically, such as in the form of a cream or ointment; or rectally such as in the form of suppositories; in dosage unit formulations containing non-toxic, pharmaceutically acceptable carriers or vehicles. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as a tablet, capsule, solution or suspension containing about 1 to about 500 mg per unit dosage of a compound or mixture of compounds represented by formula I or in a topical form containing, for example, 0.01 to 5% by weight compound represented by formula I, one to five treatments per day. Particular embodiments include, but are not limited to, 1 mg, 5 mg, 10 mg, 25 mg, 100 mg, 250 mg and 500 mg unit dosage forms.

In specific embodiments, it may be desirable to administer one or more compounds or pharmaceutical compositions of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the primary cancer, metastasis, or solid tumor.

Determination of in vivo and in vitro actvity

The compounds of the present invention can be demonstrated to inhibit primary cancer, metastasis tumor cell proliferation, solid tumor proliferation, cell transformation and tumorigenesis in vitro and in vivo using a variety of assays known in the art, or described herein (Borzilleri et al., *J. Amer. Chem. Soc.*, Vol. 122, 8890 (2000); Lee et al., *An Epothilone Analog Possessing Potent Activity Against Paclitaxel-Sensitive and -Resistant Human Tumors Book of Abstracts*, 91$^{st}$ Annual Meeting of the American Association for Cancer Research, San Francisco, Calif., Apr. 1–5, 2000; American Association for Cancer Research, Philadelphia, Pa., 2000, LB-34; Lee et al., *Clin. Cancer Res.*, Vol. 7, 1429 (2001)). Such activity can be demonstrated in an in vitro assay by contacting the compounds of the present invention with human cancer cells. In general, human cancer cells are exposed to varying concentrations of the compounds of the present invention, followed by measuring cell survival relative to controls (Borzilleri et al., Id.). Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc).

The compounds of the present invention can also be demonstrated to alter cell-proliferation in cultured cells in vitro using methods which are well known in the art. Specific examples of cell-culture models for primary brain cancer and brain metastasis include, but are not limited to, those found in the following U.S. Pat. Nos.: 6,194,158; 6,051,376 and 6,071,696, each of which is incorporated herein by reference.

The compounds of the present invention can also be demonstrated to inhibit cell transformation (or progression to malignant phenotype) in vitro. In this embodiment, cells with a transformed cell phenotype are contacted with one or more compounds of the present invention, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology*, 3d Ed., John Wiley & Sons, New York, pp. 436–446).

Loss of invasiveness or decreased adhesion may also be used to demonstrate the anti-cancer effects of the compounds of the present invention. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., *Science*, Vol. 278, 1464–66 (1997)).

The compounds of the present invention can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in *Harrison's Principals of Internal Medicine*, 13th Ed., Isselbacher et al., eds., McGraw-Hill, New York, p. 1814, and Lovejoy et al., 1997, *J. Pathol.* 181:130–135. In particular, the utility of the compounds of the present invention can be demonstrated via its effects on human tumor xenografts in athymic mice (Lee et al., *An Epothilone Analog Possessing Potent Activity Against Paclitaxel-Sensitive and -Resistant Human Tumors* Book of Abstracts, 91$^{st}$ Annual Meeting of the American Association for Cancer Research, San Francisco, Calif., Apr. 1–5, 2000; American Association for Cancer Research, Philadelphia, Pa., 2000, LB-34; Lee et al., *Clin. Cancer Res.*, Vol. 7, 1429 (2001)). Further, general animal models applicable to many types of cancer have been described, including, but not restricted to, the p53-deficient mouse model (Donehower, 1996, *Semin. Cancer Biol.* 7:269–278), the Min mouse (Shoemaker et al., 1997, *Biochem. Biophys. Acta*, 1332:F25–F48), and immune responses to tumors in rat (Frey, 1997, *Methods*, 12:173–188).

For example, a compound of the present invention can be administered to a test animal, preferably a test animal predisposed to develop a primary tumor, and the test animal subsequently examined for an decreased incidence of tumor formation in comparison with controls not administered the compound. Alternatively, a compound of the present invention can be administered to test animals having primary tumors (e.g., animals in which tumors have been induced by introduction of malignant, neoplastic, or transformed cells, or by administration of a carcinogen) and subsequently examining the tumors in the test animals for tumor regression in comparison to control animals not administered the compound. Additional in vitro assays are described in the examples below.

In Vitro Tubulin Polymerization Assay

Twice cycled (2x) calf brain tubulin is prepared following the procedure of Williams and Lee (Williams, R. C., Jr. and Lee, J. C., *Methods in Enzymology*, 85, 376–385 (1982)) and stored in liquid nitrogen before use. Quantification of tubulin polymerization potency is accomplished following a modification of the procedure described by Swindell, C. S., et al., in *J. Med. Chem.*, 34, 1176–1184 (1991). The modification used, in part, results in the expression of tubulin polymerization potency as an effective concentration for any given compound.

In accordance with this method, differing concentrations of a compound to be studied are mixed with a polymerization buffer (0.1 M MES [2(4-morpholino) ethanesulfonic acid], 1 mM EGTA [ethyleneglycol-bis-(beta-aminoethyl ether) N,N'-tetraacetic acid], 0.5 mM $MgCl_2$, pH 6.6) and added to the prepared tubulin, also mixed with a corresponding polymerization buffer, both mixtures being at 37° C. The resulting mixture is then placed in the microcuvette wells of an ultraviolet spectrophotometer (Beckman Instruments, Model DU 7400). Generally, a final microtubule protein concentration of 1.0 mg/mL and compound concentrations of 2.5, 5.0, and 10 $\mu$M are used in this procedure.

Initial slopes of OD change measured every ten seconds are calculated by the software program accompanying the spectrophotometer after initial and final times of the linear region encompassing at least three time points are manually measured. Under the prescribed conditions linear variances are generally <$10^{-6}$, slopes range from 0.03 to 0.002 absorbance units/minute, and the maximum absorbance is 0.15 absorbance units.

Effective concentration ($EC_{0.01}$) is defined as the interpolated concentration capable of inducing an initial slope of 0.01 OD/minute rate and is calculated using the formula: $EC_{0.01}$=concentration/slope $EC_{0.01}$ values are expressed as the mean with standard deviation obtained from three different concentrations. $EC_{0.01}$ values for the compounds of the invention range from 0.01 to 1000 $\mu$M.

In Vitro Cytotoxicity Assay

Cytotoxicity is assessed in HCT-116 human colon carcinoma cells by the MTS (3-(4,5-dimethylthiazol-2-yl)-5-(3-carboxymethoxyphenyl)-2-(4-sulphenyl)-2H-tetrazolium, inner salt) assay of Riss et al., *Mol. Biol. Cell*, 3(Suppl.), 184 (1992).

According to this assay, the HCT-116 human colon carcinoma cells are plated at 4,000 cells/well in 96 well microtliter plates. Twenty-four hours after plating, the compound(s) to be studied are added and serially diluted. The cells are then incubated at 37° C. for 72 hours. After incubation, MTS (at a final concentration of 333 $\mu$g/mL) and an electron coupling agent (25 $\mu$M phenazine methosulfate) are added to the cells.

A dehydrogenase enzyme in live cells reduces the MTS to a form that absorbs light at 492 nM, which can be quantified spectrophotometrically. Absorbance is directly proportional to the number of live cells, i.e. the greater the absorbance, the greater the number of live cells present. Results are expressed as IC 50 values which range from 0.01 to 1000 nM. IC 50 is the drug concentration required to inhibit cell proliferation (i.e., absorbance at 450 nM) to 50% of that of untreated control cells.

In a preferred embodiment, IC 50 values for compounds of the invention are in the range of 0.01 to 1000 nM in the in vitro cytotoxicity assay, however, compounds with activity outside of this range are included in certain embodiments.

General Methods of Preparation

Compounds of the invention can be prepared from the starting compounds designated and by the general methods described in the following schemes. The starting compounds are known materials and can be obtained by a fermentation process as described, for example, in Hofle,G., et al, *Angew. Chem. Int. Ed. Engl.*, Vol. 35, No. 13/14, 1567–1569 (1996); by semisynthesis from known epothilone starting materials as described, for example, by Vite, G., et al., in WO 99/02514 or Borzilleri et al., *J. Amer. Chem. Soc.*, Vol. 122, 8890 (2000); or by total synthesis from known starting materials as described, for example, by Nicolaou, K. C., et. al, *Angew. Chem., Int. Ed.*, Vol. 37(15), 2014–2045 (1998) or Danishefsky, S. J. et al.,*Angew. Chem. Int. Ed.* Engl., Vol. 35, 2801 (1996). All substituents are as defined in the schemes that follow or as defined above.

Compounds represented by formula I can be prepared as shown in Scheme 1.

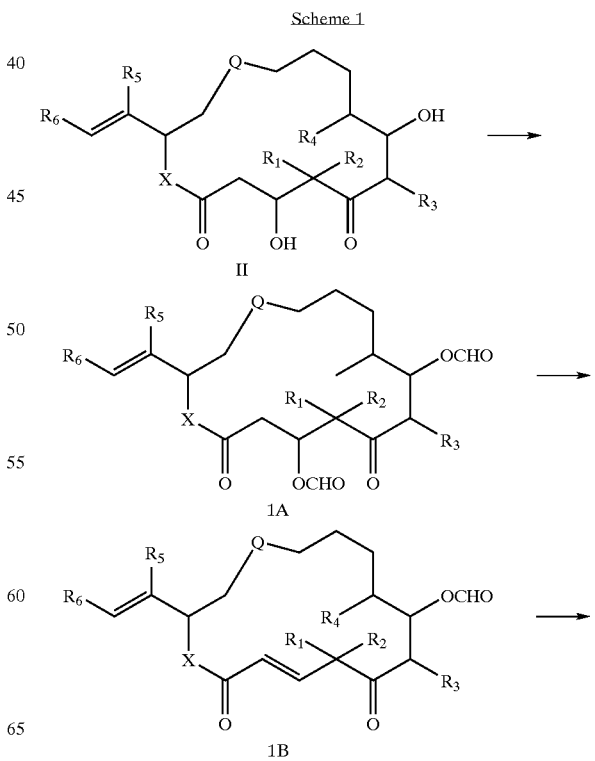

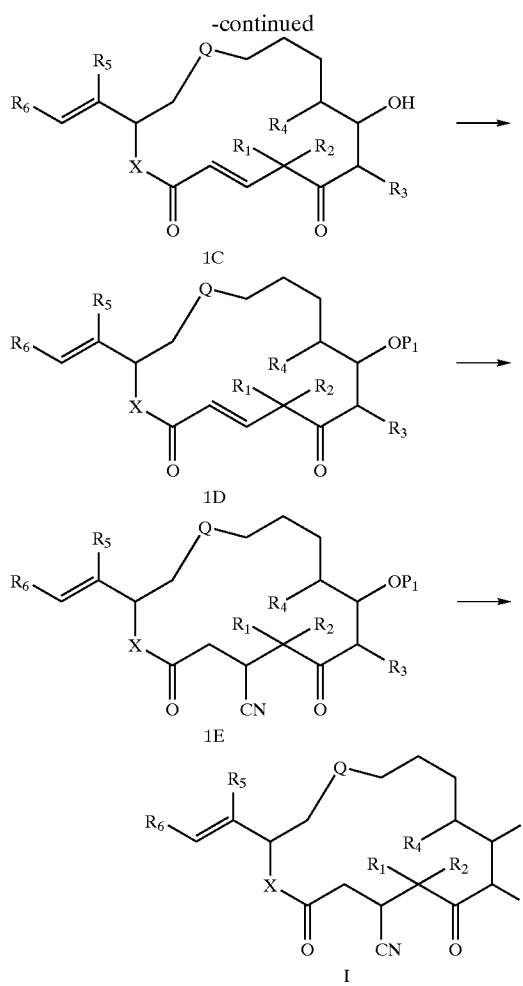

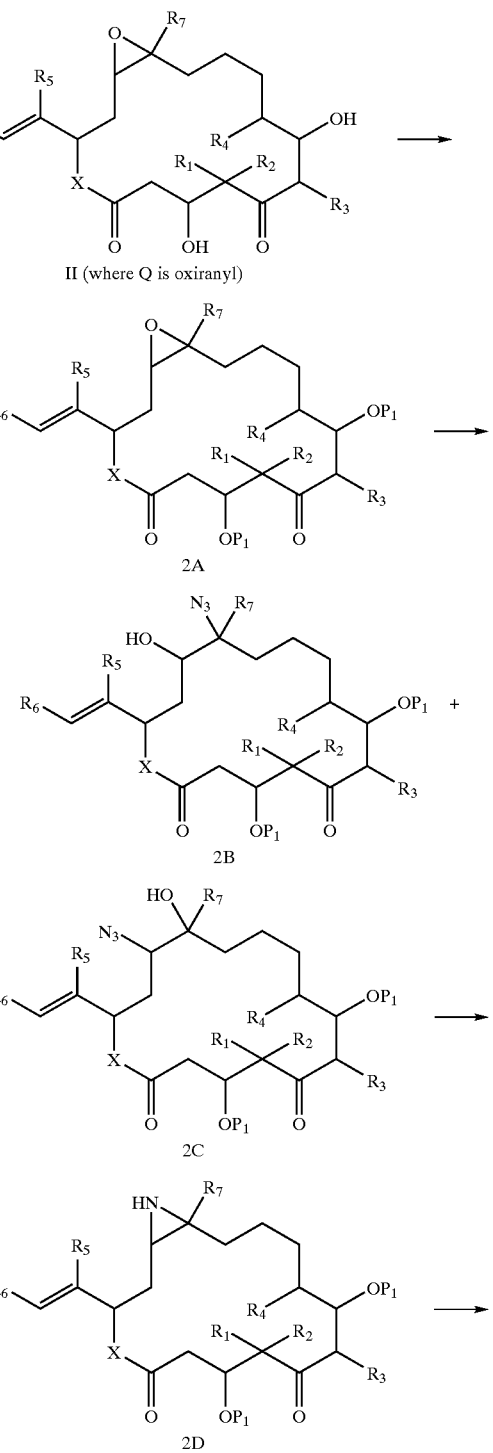

Compounds represented by formula I can be prepared from compounds represented by formula II as outlined in Scheme 1. The preparation of compounds represented by formnula II will be discussed below. The compound of formula 1A, can be prepared from a compound of formula II under standard reaction conditions with formic acid, triethylamine and acetic anhydride in dichioromethane. The compound represented by formula 1A is converted to a compound represented by formula 1B by an elimination reaction with 1,8-diazabicyclo[5.4.0]undec-7-ene in dichioromethane as taught, for example, in WO 97/19086. Removal of the formate group in compound 1B by reaction with ammonia in methanol yields a compound represented by formula 1C.

The compound represented by formula 1D, where $P_1$ is an oxygen protecting group, can be prepared from a compound represented by formula 1C by methods known to those skilled in the art such as described, for example, by Corey, E. J. and Venkateswarlu, A., *J. Am. Chem. Soc.*, (1972) 94, 6190. Compounds represented by formula 1E can be prepared from a compound represented by formula 1D by treatment with potassium cyanide in dimethyl formamide. Deprotection of a compound of formula 1E, where the protecting group represented by $P_1$ is for example, triethylsilyl, can be carried out using a 2:1:1 solution of acetic acid, tetrahydrofuran, and water or hydrogen fluoride-pyridine thereby providing a compound represented by formula I.

Compounds represented by formula II wherein Q is oxyranyl, i.e., wherein Q is represented by the first structure given above and M is O, may be synthesized from a fermentation process as described in Hofle, G., et al., *Angew. Chem. Int. Ed. Engl.*, 1996, 35, No. 13/14, 1567–1569, or by total synthesis as described in Nicolaou, K. C., et al., *Angew. Chem Int. Ed. Engl.*, 1998, 37, 2014–2045.

Scheme 2

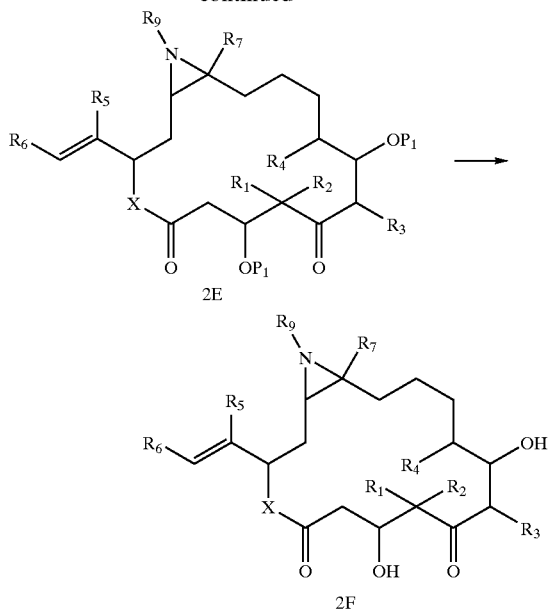

2E

2F

Scheme 2 illustrates the synthesis of compounds represented by formula II where Q is an aziridinyl group, i.e., wherein Q is represented by:

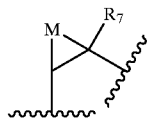

and M is $NR_9$. A compound represented by formula 2A, where $P_1$ is an oxygen protecting group, such as triethylsilyl, can be prepared from a compound represented by formula II by known methods as discussed by Corey, E. J. and Venkateswarlu, A., *J. Am. Chem. Soc.*, (1972) 94, 6190. Compounds represented by formulae 2B and 2C are prepared by treatment with an azide such as sodium azide, in a polar solvent, such as DMF. A compound represented by formula 2D can be prepared from compounds represented by formulae 2B or 2C by the Staudinger reaction, which is discussed by Ittah, Y., et al., *J. Org. Chem.*, (1978) 43, 4271. A compound represented by formula 2E where $R_9$ is not H, can be prepared from a compound represented by formula 2D using methods known in the art. For example, a compound represented by formula 2E, where $P_1$ is a triethylsilyl group, can be treated to remove the protecting group using 10% trifluoroacetic acid in dichloromethane to provide a compound represented by formula 2F, i.e. a compound represented by formula II wherein Q is an aziridinyl group, i.e., wherein Q is represented by the structure given above and M is $NR_9$ and $R_1$ through $R_9$ are as defined above.

As shown in Scheme 3 below, compounds represented by formula II where Q is a cyclopropanyl group, i.e., wherein Q is represented by:

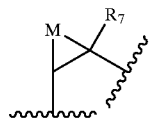

and M is $CR_{10}OR_{11}$. A compound represented by formula 3A, can be prepared by reaction of the starting material with tungsten (IV) chloride and n-butyllithium (See for example: Sharpless, K. B., et al., *J. Am. Chem. Soc.*, (1972) 94, 6190). A compound represented by formula 3B can be prepared from a compound represented by formula 3A by methods known in the art, see for example Corey, E. J. and Venkateswarlu, A. *J. Am. Chem. Soc.*, (1972) 94, 6190. A compound represented by formula 3C can be prepared from a compound represented by formula 3B by addition of a carbene group according to the method of described by Denmark, S. E., et al., *J. Org. Chem.*, (1991) 56, 6974. Deprotection of a compound represented by formula 3C, for example when $P_1$ is a triethylsilyl group, using a 2:1:1 solution of acetic acid, tetrahydrofuran, and water or hydrogen fluoride-pyridine, provides a compound represented by formula II (3D) where Q is a cyclopropane, i.e., wherein Q is represented by the second structure given above, M is $CR_{10}OR_{11}$ and $R_1$ through $R_8$, $R_9$ and $R_{10}$ are defined as described above.

Scheme 3

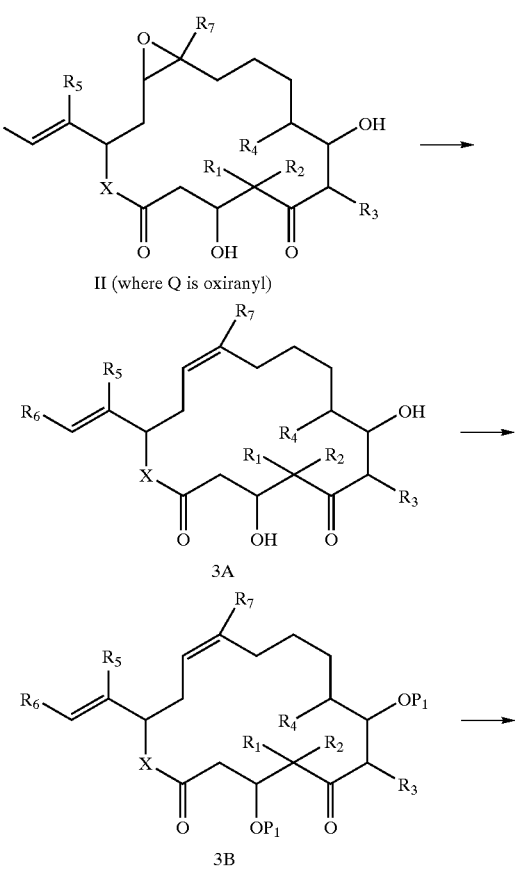

II (where Q is oxiranyl)

3A

3B

-continued

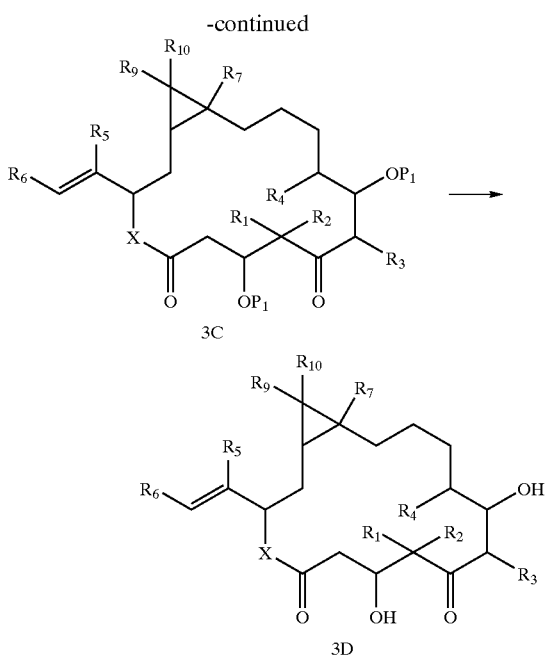

Procedures for the preparation of compounds of Schemes 2 and 3 may also be found in U.S. patent application No. 09/280,191 and Regueiro-Ren et al., Org. Lett., (2001) 3, 2693. Both of which are incorporated herein by reference in their entirety.

EXAMPLES

The following non-limiting examples serve to illustrate the practice of the invention.

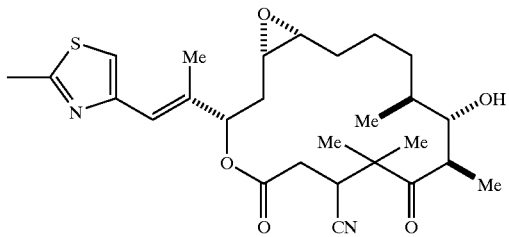

11-Hydroxy-8,8,10,12-tetramethyl-3-[1-methyl-2-(2-methyl-thiazol-4-yl)-vinyl]-5,9-dioxo-4,17-dioxa-bicyclo[14.1.0]heptadecane-7-carbonitrile Step 1: C-7 Silylation 2.52 mL of N,N-diisopropylethylamine (1.871 g, 14.475 mmol, 15 eq.) and 118 mg DMAP (N,N-dimethylaminopyridine) (0.965 mmol, 1 eq.) were added to a stirred solution of 2,3-dehydro epothilone A (459 mg, 0.965 mmol, prepared from epothilone A using the procedure described in PCT WO 97/19086 in 15 mL of dichloromethane under a nitrogen atmosphere. To the resulting mixture was added 1.62 mL triethylsilyl chloride (1.455 g, 9.650 mmol, 10 eq) and the solution was heated at 40° C. for 14 hr. The solution was allowed to cool to room temperature and subsequently poured into 60 mL of saturated aqueous sodium bicarbonate solution. The aqueous layer was extracted and washed with three 50 mL portions of dichloromethane. The combined organic layers were dried over sodium sulfate and concentrated under reduced pressure, forming a slightly brown oil. This crude material was chromatographed using silica gel eluting with 25% ethyl acetate in hexanes to afford 546 mg of C7-triethylsilyloxy-2,3-dehydro-epothilone A as a clear viscous oil (96%).

Step 2: Potassium Cyanide addition

To a stirred solution of C7-triethylsilyloxy-2,3-dehydro-epothilone A (51 mg, 0.087 mmol) in 1.6 mL dimethyl formamide under an argon atmosphere, 57 mg potassium cyanide (0.873 mmol, 10 eq.) was added. The mixture was stirred at 25° C. for 46 hr. The solvent was then removed under vacuum. The crude material was loaded onto a silica gel column and chromatographed stepwise with 15% acetonitrile/toluene then with 20% ethyl acetate/hexanes to yield the resulting product as a mixture of diastereomers, which consist of isomer A: 9.7 mg-18%, M+H=617.4 and isomer B: 10.9 mg-20%, M+H=617.4.

Step 3: Deprotection

The diastereomers of C3-cyano-C7-triethylsilyloxy-2,3-dehydroepothilone A were placed in separate flasks (9.7 mg isomer A and 10.9 mg isomer B). Each flask was stirred at RT for 48 hr. in 0.5 mL tetrahydrofuran, 0.25 mL acetic acid, and 0.25 mL $H_2O$, and purified using flash chromatography (35% ethyl acetate/hexanes) to yield 3.5 mg product isomer A (44%, M+H=503.3) as a clear oil, and 3.5 mg product isomer B (39%, M+H=503.3) as a cloudy oil.

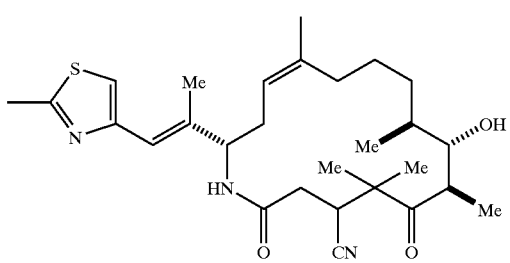

11-Hydroxy-8,8,10,12,16-pentamethyl-3-[1-methyl-2-(2-methyl-thiazol-4-yl)-vinyl]-5,9-dioxo-4,17-dioxa-bicyclo[14.1.0]heptadecane-7-carbonitrile The corresponding epothilone B analog was prepared using the procedure described in Example 1, except that 2,3-dehydro epothilone B was used as the starting material. The following yields were obtained for each step: (1) C-7 silylation (90%); (2) potassium cyanide addition (approximately 1:1 mixture of C-3 diastereomers, 65% combined yield; (3) deprotection (isomer A, 1.8 mg-53%, M+H=517; isomer B, 2.4 mg (41%), M+H=517).

8-Hydroxy-5,5,7,9,13-pentamethyl-16-[1-methyl-2-(2-methyl-thiazol-4-yl)-vinyl]-2,6-dioxo-azacyclohexadec-13-ene-4-carbonitrile The corresponding epothilone D analog was prepared using the procedure described in Example 1, except that 2,3-dehydro epothilone D was used as the starting material and was subsequently converted to the lactam through ring-opening in the presence of sodium azide followed by macrolactonization by known procedures such as that described in WO 99/27890, incorporated by reference herein.

All references with respect to synthetic, preparative and analytic procedures are incorporated herein by reference as if set forth at length herein. The present invention may be embodied in other specific forms without departing from the spirit or essential attributes thereof and, accordingly, reference should be made to the appended claims, rather than to the foregoing specification, as indicating the scope of the invention.

What is claimed is:

1. A compound represented by formula I:

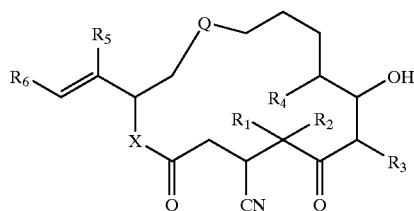

I wherein:

Q is selected from the group consisting of

M is O, $NR_9$, $CR_{10}R_{11}$;

X is O or NH;

$R_1$, $R_2$, $R_3$, $R_4$, $R_5$, $R_6$, $R_7$ and $R_8$ are independently selected from the group consisting of hydrogen or lower alkyl;

$R_6$ is selected from the group consisting of aryl, substituted aryl, and heterocyclo;

$R_7$ and $R_8$ are selected from the group consisting of hydrogen, alkyl, substituted alkyl, and cyano;

$R_9$ is selected from the group consisting of hydrogen, hydroxy, alkyl, substituted alkyl, alkoxy, substituted alkoxy, substituted aryl, cycloalkyl, heterocyclo, $R_{12}C=O$, $R_{13}OC=O$, $R_{14}SO_2$, $R_{15}R_{16}NC=O$, $R_{17}R_{18}NSO_2$, and $NR_{19}R_{20}$;

$R_{10}$ and $R_{11}$ are independently selected from the group consisting of hydrogen, halogen, hydroxy, alkyl, substituted alkyl, alkoxy, substituted alkoxy, aryl, substituted aryl, cycloalkyl, heterocyclo, $R_{21}C=O$, $R_{22}OC=O$, $R_{23}NHC=O$, and $NR_{24}R_{25}$; and $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$ are independently selected from the group consisting of hydrogen, alkyl, substituted alkyl, aryl, substituted aryl, and heterocyclo with the proviso that $R_{13}$ and $R_{14}$ cannot be hydrogen;

$R_{15}$ and $R_{16}$, $R_{17}$ and $R_{18}$, $R_{19}$ and $R_{20}$, $R_{24}$ and $R_{25}$ can each independently be taken together to form a heterocyclic ring; and somers, clathrates, prodrugs, pharmaceutically acceptable salts, solvates or hydrates thereof.

2. A compound which is a regioisomer or stereoisomer of a compound of claim 1 or pharmaceutically acceptable salts, solvates or hydrates thereof.

3. The compound of claim 1 wherein $R_6$ is selected from the group consisting of:

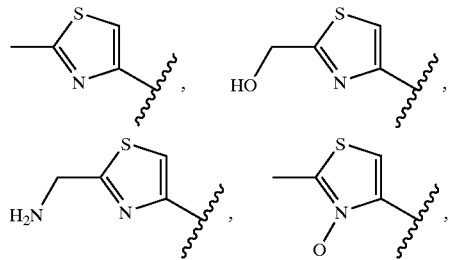

pyrrolidinyl, pyrrolyl, indolyl, pyrazolyl, imidazolyl, oxazolyl, oxazolidinyl, thiazolyl, furyl, thienyl, piperidinyl, piperazinyl, azepinyl, pyridyl, pyrazinyl, pyrimidinyl, morpholinyl, thietanyl, thiiranyl, triazinyl, and triazolyl or pharmaceutically acceptable salts, solvates or hydrates thereof.

4. The compound of claim 1 wherein X is O.

5. The compound of claim 1 wherein X is NH.

6. The compound of claim 1 wherein M is O.

7. The compound of claim 1 wherein M is $NR_9$.

8. The compound of claim 1 wherein M is $CR_{10}R_{11}$.

9. The compound of claim 1 wherein said compound is selected from the group consisting of:

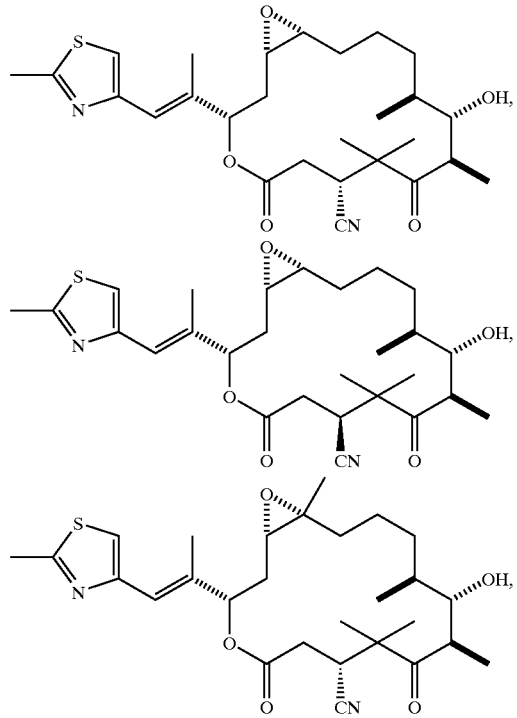

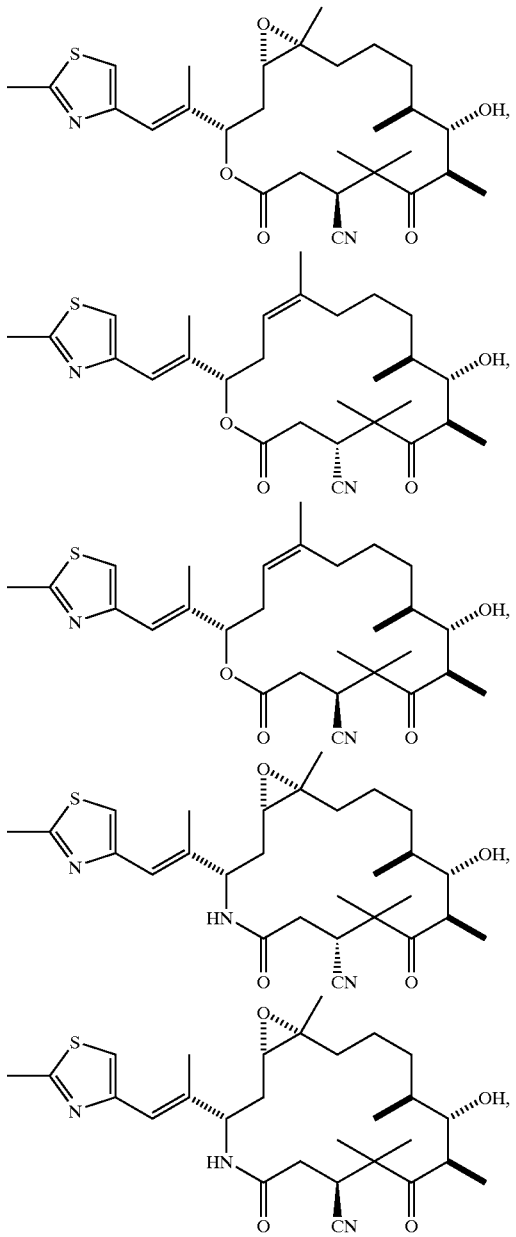

and mixtures or pharmaceutically acceptable salts, solvates or hydrates thereof.

10. The compound of claim 1 wherein said compound is selected from the group consisting of:
   11-Hydroxy-8,8,10,12-tetramethyl-3-[1-methyl-2-(2-methyl-thiazol-4-yl)-vinyl]-5,9-dioxo-4,17-dioxabicyclo[14.1.0]heptadecane-7-carbonitrile;
   11-Hydroxy-8,8,10,12,16-pentamethyl-3-[1-methyl-2-(2-methyl-thiazol-4-yl)-vinyl]-5,9-dioxo-4,17-dioxabicyclo[14.1.0]heptadecane-7-carbonitrile; and
   8-Hydroxy-5,5,7,9,13-pentamethyl-16-[1-methyl-2-(2-methyl-thiazol-4-yl)-vinyl]-2,6-dioxo-azacyclohexadec-13-ene-4-carbonitrile;
and pharmaceutically acceptable salts, solvates or hydrates thereof.

11. A pharmaceutical composition comprising as an active ingredient at least one compound of claim 1, or a pharmaceutically acceptable salt thereof, and one or more pharmaceutically acceptable carriers, excipients and diluents.

12. The pharmaceutical composition of claim 11 additionally comprising as a further active ingredient a therapeutic agent useful in the treatment of cancer or other proliferative diseases.

13. The pharmaceutical composition of claim 12 wherein said therapeutic agent useful in the treatment of cancer or other proliferative diseases is selected from the group consisting of adriamycin, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, Chloroambucil, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, thiotepa, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenoloc acid, daunorubicin, deferoxamine, floxuridine, doxifluridine, ratitrexed, idarubicin, epirubican, pirarubican, zorubicin, mitoxantrone, bleomycin sulfate, mitomycin C, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, verapamil, VP-16, altretamine, thapsigargin and topotecan.

14. A method for treating cancer or other proliferative diseases in a mammal in need thereof which comprises administering an effective amount of at least one compound of claim 1, or a pharmaceutically acceptable salt, solvate or hydrate thereof to said mammal.

15. The method of claim 14 wherein said cancer is responsive to microtubule-stabilization.

16. A method for inhibiting angiogenesis in a mammal in need thereof which comprises administering an effective amount of at least one compound of claim 1, or a pharmaceutically acceptable salt, solvate or hydrate thereof to said mammal.

17. A method for inducing apoptosis in a mammal in need thereof which comprises administering an effective amount of at least one compound of claim 1, or a pharmaceutically acceptable salt, solvate or hydrate thereof to said mammal.

18. The method of claim 14 wherein said compound of claim 1 is administered simultaneously or sequentially with a therapeutic agent useful in the treatment of cancer or other proliferative diseases.

19. The method of claim 18 wherein said compound of claim 1 is administered prior to the administration of the therapeutic agent.

20. The method of claim 18 wherein said compound of claim 1 is administered after the administration of the therapeutic agent.

21. The method of claim 18 wherein said therapeutic agent useful in the treatment of cancer or other proliferative diseases is selected from the group consisting of adriamycin, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, Chloroambucil, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, thiotepa, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenoloc acid, daunorubicin, deferoxamine, floxuridine, doxifluridine, ratitrexed, idarubicin, epirubicin, pirarubican, zorubicin, mitoxantrone, bleomycin sulfate, mitomycin C, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, verapamil, VP-16, altretamine, thapsigargin and topotecan.

22. The method of claim 14 wherein said compound of claim 1 is administered simultaneously or sequentially with a therapeutic agent useful inhibiting angiogenesis.

23. The method of claim 22 wherein said compound of claim 1 is administered prior to the administration of the therapeutic agent.

24. The method of claim 22 wherein said compound of claim 1 is administered after the administration of the therapeutic agent.

25. The method of claim 22 wherein said therapeutic agent useful in inhibiting angiogenesis is selected from the group consisting of indolinethiones, pyridopyrimidines, quinoazolines, phenyl-pyrrolo-pyrimidines, trastuzumab, IMC-C225, AG 1571 (SU 5271), SU 5416, SU 6668, Interferon-alpha, Interleuken-12, IM 862, EMD-121974, calcium influx inhibitor (CAI), neomycin, squalamine, endostatin, SI-27, MMI-166, marimastat, BAY-129556, prinomastat (AG-3340), metastat (COL-3), CGS-27023A and BMS-275291.

26. The method of claim 14 wherein said mammal is human.

27. The method of claim 16 wherein said mammal is human.

28. The method of claim 17 wherein said mammal is human.

29. The method of claim 14 wherein said cancer is a cancer of the brain, breast, central nervous system, stomach, bladder, prostate, colon, rectum, liver, lung (both small cell and non-small cell), pancreas, esophagus, mouth, pharynx, kidney, bone, pituitary, ovary, uterine, skin, head and neck, cervix or larynx.

30. The method of claim 14 wherein said cancer is a solid tumor.

31. The method of claim 14 wherein said cancer is a metastatic tumor.

32. A unit dosage form comprising a compound of claim 1.

33. A sterile injectable unit dosage form comprising a compound of claim 1.

34. The unit dosage form of claim 32 wherein said dosage form is lyophilized.

35. The unit dosage form of claim 33 wherein said dosage form is lyophilized.

* * * * *